United States Patent [19]

Landa

[11] Patent Number: 5,020,909

[45] Date of Patent: Jun. 4, 1991

[54] "IN-LINE" SPECTRAL REFERENCE METHOD FOR SPECTROMETERS

[76] Inventor: Issac J. Landa, 7616 Fontaine St., Potomac, Md. 20854

[21] Appl. No.: 487,041

[22] Filed: Mar. 2, 1990

[51] Int. Cl.⁵ ............................................. G01J 3/42
[52] U.S. Cl. .................................. 356/300; 356/326; 356/243
[58] Field of Search ............... 356/300, 319, 323, 325, 356/243, 326, 328; 250/252.1 A, 343, 351

[56] References Cited

U.S. PATENT DOCUMENTS

| | | | |
|---|---|---|---|
| Re. 27,270 | 1/1972 | Selgin | 356/243 |
| 3,861,788 | 1/1975 | Webster | 350/315 |
| 3,973,849 | 8/1976 | Jackson et al. | |
| 4,264,205 | 4/1981 | Landa | 356/326 |
| 4,285,596 | 8/1981 | Landa | 356/308 |
| 4,529,308 | 7/1985 | Rife | 356/323 |
| 4,937,448 | 6/1990 | Mantz et al. | 356/325 |

Primary Examiner—F. L. Evans
Attorney, Agent, or Firm—Sterne, Kessler, Goldstein & Fox

[57] ABSTRACT

An in-line spectral method adapted for use with a single-beam reference spectrometer scanning a sample, the method comprising the steps of (a) scanning with a single-beam spectrometer (b) rotating a wheel in synchronization and in an optical path with the single-beam spectrometer of step (a), the wheel having open alternating with segments comprising reference material, (c) producing with step (b) alternate spectral scans as of the spectrometer and the sample, and of the spectrometer, the sample and said reference material, (d) comparing said spectral scans of step (c) in order to extract the spectrum of said reference material; and (e) using said extracted spectrum for real-time, dynamic spectral compensation, to result in absolute correct sample spectrum.

1 Claim, 1 Drawing Sheet

"IN-LINE" SPECTRAL REFERENCE METHOD FOR SPECTROMETERS

SUMMARY OF THE INVENTION

The present invention is a method of introducing a reference material into the optical path of a single-beam spectrometer in order to dynamically measure the superimposed absorption spectrum of the reference material in real-time and to use this spectrum for the purpose of spectral calibration and drift compensation.

DETAILED DESCRIPTION OF THE PRESENT INVENTION

Figure 1:
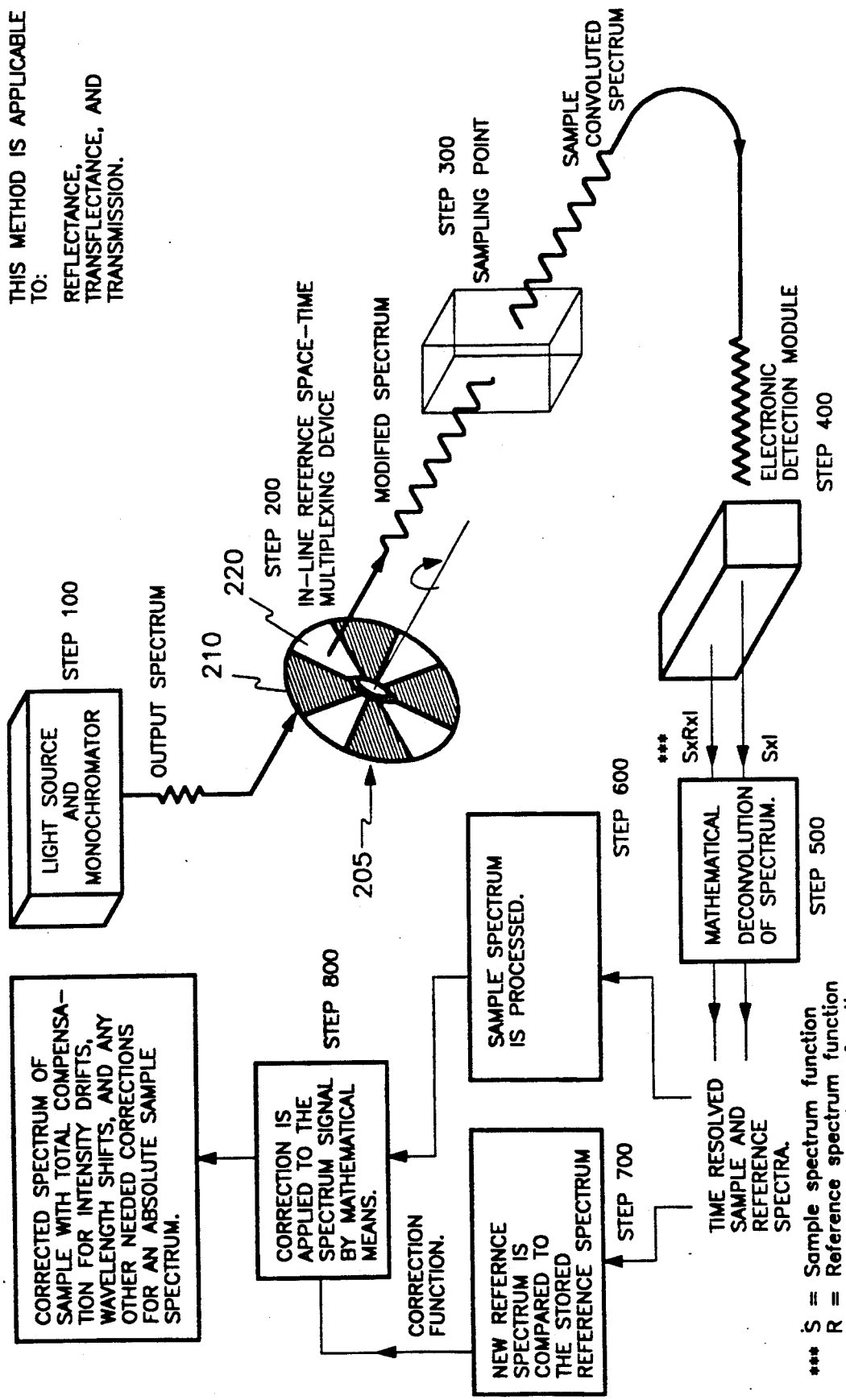
FIG. 1 is a flow diagram illustrating the present invention.

Chief among the advantages of this approach is that a dedicated optical beam for reference is not required. In addition, the entire optical system, including the sample and sampling accessories, are included in the calibration and compensation loop.

This "in-line" reference is implemented with a rapidly rotating wheel 205 external to the monochromator, placed in the optical path. Wheel 205 is fabricated such that "open" segments 220 alternate with segments 210 composed of the reference material. The reference material (typically, but not limited, to polystyrene) is largely transparent with a predetermined distinctive and stable absorption spectrum.

The method of the present invention is set forth in FIG. 1. Generally, rotation of the wheel 205 is synchronized with the scanning of monochromator to acquire alternating spectral scans, first of the instrument and sample only; and, second of the instrument, sample and reference material. These spectra are compared in such a way to extract the spectrum of the reference material alone from the total spectrum, and use the information contained in this reference spectrum for real-time, dynamic spectral calibration and drift compensation.

More specifically, step 100 of the method involves the emission of light samples using a monochromator. In step 200, the wheel 205 is synchronized with the scanning of monochromator 100 to acquire alternating spectral scans, first of the instrument and sample only; and, second of the instrument, sample and reference material output spectrum is scanned with alternately spaced material. In step 300, the output is sampled and detected by an electronic detection module in Step 400. In step 500, the converted electrical signal undergoes mathematical deconvolution. In step 600, the new reference spectrum is compared to the stored reference spectrum. In step 700, the sample spectrum is processed. In step 800, correction is applied to the spectrum signal by mathematical means. The result is a corrected spectrum of sample with total compensation for intensity drifts wavelength shifts, and other spectral distortions.

The reference spectra obtained in this matter is useful for wavelength calibration. It is also clear that the applicability of this "in-line" technique for dynamic drift compensation, which requires less fundamental and more complicated algorithmic approaches can be achieved with chemometrics implementation including Partial Least Squares (PLS), Principle Component Analysis (PCR), etc. This concept has been first proposed for implementation and defined in 1989.

There are many other applications for this type of method. The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

I claim:

1. An in-line spectral method adapted for use with a single-beam references spectrometer scanning a sample, the method comprising the steps of:
   (a) scanning a sample with a single-beam spectrometer;
   (b) rotating a filter wheel in synchronization with the single-beam spectrometer of step (a), said wheel having open segments alternating with segments comprising reference material, said reference material being largely transparent with a predetermined absorption spectrum, said wheel placed in the optical path of the spectrometer;
   (c) producing with step (b) alternate spectral scans as follows:
      (i) of the spectrometer and the sample, and
      (ii) of the spectrometer, the sample and said reference material;
   (d) comparing said spectral scans of step (c) in order to extract the spectrum of said reference material; and
   (e) using said extracted spectrum for real-time, dynamic spectral compensation to result in absolute correct sample spectrum.

* * * * *